US011275140B2

(12) United States Patent
Vesanen et al.

(10) Patent No.: US 11,275,140 B2
(45) Date of Patent: Mar. 15, 2022

(54) EMULATION MODE FOR MRI

(71) Applicant: KONINKLIJKE PHILIPS N.V., Eindhoven (NL)

(72) Inventors: Panu Tapani Vesanen, Helsinki (FI); Lizette Warner, Arlington, TX (US); Jukka Ilmari Tanttu, Vantaa (FI)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/979,198

(22) PCT Filed: Mar. 11, 2019

(86) PCT No.: PCT/EP2019/056029
§ 371 (c)(1),
(2) Date: Sep. 9, 2020

(87) PCT Pub. No.: WO2019/175110
PCT Pub. Date: Sep. 19, 2019

(65) Prior Publication Data
US 2020/0408866 A1    Dec. 31, 2020

Related U.S. Application Data

(60) Provisional application No. 62/641,583, filed on Mar. 12, 2018.

(30) Foreign Application Priority Data

Apr. 5, 2018 (EP) .................................. 18165858

(51) Int. Cl.
*G01R 33/54* (2006.01)
*A61B 5/00* (2006.01)
*A61B 5/055* (2006.01)
*A61N 5/10* (2006.01)
*G01R 33/24* (2006.01)
(Continued)

(52) U.S. Cl.
CPC .......... *G01R 33/543* (2013.01); *A61B 5/0036* (2018.08); *A61B 5/055* (2013.01);
(Continued)

(58) Field of Classification Search
USPC ......................................................... 324/309
See application file for complete search history.

(56) References Cited

U.S. PATENT DOCUMENTS 7,948,235 B2 *   5/2011   Foxall ................ G01R 33/4616
                                                             324/307
10,698,062 B2   6/2020   Yang et al.
(Continued)

OTHER PUBLICATIONS

International Search Report and Written Opinion From PCT/EP2019/056029 dated Jun. 28, 2019.
(Continued)

*Primary Examiner* — Rodney E Fuller

(57) ABSTRACT

A magnetic resonance imaging system is configured to be selectively operated in a default mode and an emulation mode. Execution of machine executable instructions by a processor of the magnetic resonance imaging system causes the magnetic resonance imaging system to receive a selection signal selecting the emulation mode. The magnetic resonance imaging system switches from the default mode to the emulation mode. The magnetic resonance imaging system is operated in the emulation mode using the set of emulation control parameters. The emulated magnetic resonance imaging data is acquired from the imaging zone of the magnetic resonance imaging system.

14 Claims, 4 Drawing Sheets

(51) Int. Cl.
| | |
|---|---|
| G01R 33/44 | (2006.01) |
| G01R 33/48 | (2006.01) |
| G01R 33/483 | (2006.01) |
| G01R 33/485 | (2006.01) |
| G01R 33/50 | (2006.01) |
| G01R 33/56 | (2006.01) |

(52) U.S. Cl.
CPC ......... *A61N 5/1039* (2013.01); *G01R 33/246* (2013.01); *G01R 33/443* (2013.01); *G01R 33/485* (2013.01); *G01R 33/4828* (2013.01); *G01R 33/4838* (2013.01); *G01R 33/50* (2013.01); *G01R 33/5608* (2013.01); *G01R 33/546* (2013.01)

(56) References Cited

U.S. PATENT DOCUMENTS

| | | |
|---|---|---|
| 2004/0169512 A1 | 9/2004 | Jara |
| 2010/0103165 A1 | 4/2010 | Lee et al. |
| 2010/0103166 A1 | 4/2010 | Warntjes |
| 2011/0280456 A1 | 11/2011 | Sussman et al. |
| 2013/0134975 A1 | 5/2013 | Nehrke et al. |
| 2016/0310761 A1 | 10/2016 | Li et al. |
| 2017/0315200 A1 | 11/2017 | Kiefer et al. |
| 2019/0361082 A1* | 11/2019 | Hess ................. G01R 33/5676 |

OTHER PUBLICATIONS

Sh0an C. Kale et al: "Optimization of the SNR-resolution tradeoff for registration of magnetic resonance images", Human Brain Mapping, vol. 29, No. 10, Oct. 23, 2007 (Oct. 23, 2007), pp. 1147-1158.

Xanthis Christos G et al: "MRISIMUL: A GPU-Based Parallel Approach to MRI Simulations", IEEE Transactions on Medical Imaging, IEEE Service Center, Piscataway, NJ, US, vol. 33, No. 3, Nov. 20, 2013 (Nov. 20, 2013), pp. 607-617.

* cited by examiner

EMULATION MODE FOR MRI

CROSS REFERENCE TO RELATED APPLICATIONS

This application is a U.S. national phase application of International Application No. PCT/EP2019/056029 filed Mar. 11, 2019, which claims the benefit of U.S. Provisional Application Ser. No. 62/641,583 filed Mar. 12, 2018 and EP Application Serial No. 18165858.4 filed Apr. 5, 2018 and is incorporated herein by reference.

FIELD OF THE INVENTION

The invention relates to the field of magnetic resonance imaging.

BACKGROUND OF THE INVENTION

A large static magnetic field is used by Magnetic Resonance Imaging (MRI) systems, also referred to as MRI scanners, to align the nuclear spins of atoms as part of the procedure for producing images within the body of a patient. This large static magnetic field is referred to as the B0 field.

During an MRI scan, Radio Frequency (RF) pulses generated by a transmitter coil cause perturbations to the local magnetic field and RF signals emitted by the nuclear spins are detected by a receiver coil. These RF signals are used to construct MRI images. These coils can also be referred to as antennas. Further, the transmitter and receiver coils can also be integrated into a single transceiver coil that performs both functions. It is understood that the use of the term transceiver coil also refers to systems where separate transmitter and receiver coils are used. The transmitted RF field is referred to as the B1 field.

MRI scanners are able to construct images of either slices or volumes. A slice is a thin volume that is only one voxel thick. A voxel is a small volume over which the MRI signal is averaged, and represents the resolution of the MRI image. A voxel may also be referred to as a pixel herein.

For different applications different MRI systems with different MRI scanners are used. Different hardware features may result in differing image characteristics. For example, the filed strengths of the static magnetic fields, i.e. B0 fields, generated by different MRI scanners may significantly differ, resulting in magnetic resonance images with different imaging characteristics. Commercial MRI systems may e.g. be available with B0 fields in the range of 0.2 T to 7 T.

SUMMARY OF THE INVENTION

The invention provides for a magnetic resonance imaging system, a computer program product, and a method in the independent claims. Embodiments are given in the dependent claims.

In one aspect, the invention relates to a magnetic resonance imaging system. The magnetic resonance imaging system comprises a main magnet for generating a main magnetic field within an imaging zone of the magnetic resonance imaging system, a magnetic field gradient system for generating a spatially dependent gradient magnetic field within the imaging zone, a radio-frequency antenna system configured for acquiring magnetic resonance imaging data from the imaging zone.

The magnetic resonance imaging system further comprises a memory storing machine executable instructions, a set of default control parameters for operating the magnetic resonance imaging system in a default mode for acquiring magnetic resonance imaging data for reconstructing a magnetic resonance image with a set of default imaging characteristics and a set of emulation control parameters for operating the magnetic resonance imaging system in an emulation mode for acquiring emulated magnetic resonance imaging data for reconstructing an emulated magnetic resonance image with a set of emulated imaging characteristics mimicking a set of reference imaging characteristics assigned to a reference magnetic resonance imaging system. The reference imaging characteristics differ from the default imaging characteristics.

The magnetic resonance imaging system further comprises a processor. Execution of the machine executable instructions by the processor causes the processor to control the magnetic resonance imaging system to receive a selection signal selecting the emulation mode. The magnetic resonance imaging system switches from the default mode to the emulation mode. The magnetic resonance imaging system is operated in the emulation mode using the set of emulation control parameters. The emulated magnetic resonance imaging data is acquired from the imaging zone of the magnetic resonance imaging system.

Embodiments may have the beneficial effect that the magnetic resonance imaging system may be operable in at least two modes, i.e. a default mode and emulation mode. The default mode may be optimized for obtaining MRI images with the best possible image quality based on the hardware features provided by the MRI system. These MRI mages may e.g. be intended for diagnostic purposes. For example, the signal-to-noise ratio of the resulting MRI images may be maximized. In contrast, the emulation mode may be configured to obtain emulated MRI images with emulated imaging characteristics mimicking reference imaging characteristics assigned to a reference magnetic resonance imaging system. The reference imaging characteristics may be characteristics of MRI images acquired by the reference magnetic imaging system operated in a default mode. The default mode of the reference magnetic imaging system may be optimized for obtaining reference MRI images with the best possible image quality based on the hardware features provided by the reference MRI system. Thus, the emulation mode may not be optimized for obtaining MRI images with the best possible image quality based on the hardware features provided by the MRI system, but rather for obtaining MRI images with imaging characteristics resembling the imaging characteristics of MRI images obtained by the reference magnetic resonance imaging system as close as possible.

The reference magnetic resonance imaging system may e.g. be used to check and/or adjust a position of an anatomical structure of interest. The respective position may e.g. be defined by the emulated magnetic resonance image. A high similarity of imaging characteristics of the emulated magnetic resonance image defining the position and (reference) imaging characteristics of the magnetic resonance images provided by the reference magnetic resonance imaging system may alleviate the check and/or adjustment of a current position determined by magnetic resonance images of the reference magnetic resonance imaging system with respect to the position defined by the emulated magnetic resonance image. The emulated magnetic resonance image may be provided to the reference magnetic resonance imaging system, e.g. in order to define a position of an anatomical structure of interest to be achieved.

The emulated magnetic resonance image may e.g. be used for simulating a radiation delivery and/or establishing a dose plan. The reference magnetic resonance imaging system may e.g. be used for position an anatomical structure of interest for delivering the simulated radiation and/or execution of the respective dose plan.

The magnetic resonance imaging system may provide a menu, e.g. by a user interface like a display, comprising different options for selection. The option may comprise one or more default modes as well as one or more emulation modes. The default modes may e.g. be optimized for different types of anatomical structures of interest to be imaged. According to embodiments, each of the emulation modes may e.g. be assigned to a different reference magnetic imaging system. According to embodiments, multiple emulation modes may be assigned to different modes of the same reference magnetic imaging system. For example, the respective reference magnetic imaging system may be configured to be operated in different (default) modes and for each of those operation modes of the reference magnetic imaging system, the menu may provide an individual emulation mode defined by an individual set of emulation control parameters.

According to embodiments, the set of reference imaging characteristics may be stored by the magnetic resonance imaging system, e.g. in the memory. Thus, the resulting emulated imaging characteristics may be monitored in order to check, whether they accurately mimic the predefined reference imaging characteristics. For example, the degree of deviation of the emulated imaging characteristics from the reference imaging characteristics may be determined. In case the deviation is below a predefined threshold, the matching of the emulated magnetic resonance imaging data and/or the emulated magnetic resonance image may be accepted as being sufficiently accurate. According to embodiments, an optimization process may be executed in order to obtain/adjust the set of emulation control parameters in order to ensure a sufficiently accurate matching. For example, the emulation control parameters may be varied until a set of emulation control parameters is found resulting in emulated imaging characteristics sufficiently close to the desired reference imaging characteristics. According embodiment, this optimization process may e.g. be executed for a test set of emulated magnetic resonance data and the resulting emulation control parameter may be stored and used for acquisition of further emulated magnetic resonance data. For example, an image quality achieved by means of MRI systems which are optimized for acquiring magnetic resonance imaging data used for reconstruction of diagnostic images may often be higher than an image quality achievable by an MRI system which is used in combination with a radiational system, like e.g. a radiation delivery system. In the later case, e.g. additional constructional constraints may have to be observed, which may e.g. result in a smaller main magnetic field.

According to embodiments, the MRI system may be an MRI system optimized for diagnostic purposes being configured for generating a main magnetic field with a larger field strength than the reference MRI system. The reference MRI system may e.g. be part of an MRI-guided radiation delivery system. For example, the MRI system may be a 3 T MRI system used for preparing a dose plan, while the reference MRI system may be a 1.5 T MRI system, e.g. of a MRI-guided LINAC. The reference MRI system may be used for magnetic resonance imaging, when executing the prepared dose plan.

For example, in the setting of radiation therapy simulation with an MRI system and a radiation delivery with a combined MRI-guided LINAC system, there may be a need for providing images of similar image quality by both systems, despite of possible differences e.g. in operating field strength.

According to embodiments, an MRI system with a first set of hardware specifications, e.g. field strength, gradient strength, etc., is configured to acquire emulated MRI data and reconstruct emulated MRI images having emulated image properties matching image properties of MRI images reconstructed from MRI data acquired with a reference MRI system having a second set of hardware specifications different from the first set of hardware specifications.

Typically, a first MRI system used for diagnostics, treatment planning and/or radiotherapy simulation often has different hardware specifications than a second MRI system used e.g. in combination with a radiation delivery system, like a LINAC, for execution of a dose plan prepared using MRI images reconstructed using magnetic resonance imaging data acquired by the first MRI system. As a result, registration between planning MRI images and MRI images acquired for preparing the execution of the plan and/or on the fly during the execution of the plan may be challenging. According to embodiments, during the planning phase an emulated MRI image may be reconstructed that regarding the underlying imaging characteristics matches MRI images reconstructed using MRI data acquired in preparation and/or on the fly during execution of the plan. This approach may alleviate and/or improve image registration. Furthermore, time may be saved during the treatment planning phase, preparation of the execution and/or during the execution of the plan.

Considering e.g. modern radiation therapy, such a procedure is divided in separated steps, comprising radiation therapy simulation and planning as well as an execution of the respective. Traditionally, the therapy may be simulated with a CT scanner.

According to embodiments, an MRI scan may be executed in addition offering a superior soft-tissue contrast relative to the CT scan. Alternatively, an MRI-only simulation may be deployed. A CT scan however uses computer-processed combinations of a plurality of X-ray measurements taken from different angles in order to produce cross-sectional, i.e. tomographic, images of an anatomical section of interest of a scanned subject. An MRI-only planning data acquisition may have the beneficial effect that the patient is not exposed to any additional X-rays during planning. In particular, in case such planning phases have to be performed repeatedly and/or in case the patient is a child, the exposition to X-rays should be minimized as far as possible.

Consider a setting where a radiotherapy is simulated with a dedicated MRI system and the resulting dose plan executed with an MRI-guided radiation delivery system, like e.g. a LINAC system. In this setting, image quality based on the magnetic resonance imaging data provided by the two different MRI system may be inequivalent, leading to problems in e.g. image registration. The reference magnetic resonance imaging system may e.g. comprise a radiation source which may e.g. be provided in form of a linear accelerator (LINAC). Alternatively, e.g. $^{60}$Co radionuclides may be used. In order to improve e.g. verification of the patient position and adjustment of the position, MRI guidance may be used for positioning and position controlling. For example, an MRI-guided LINAC system comprising a radiation delivery system with a LINAC in combination with an MRI imaging system may be used.

Specifically, differences in SNR and contrast may be common in case of scanners operating at different field strengths, like B0 field strength, since thermal equilibrium magnetization and relaxation times are affected by the magnetic field. For example, the B0 field strength of a diagnostic MRI system may be 3 T, while the B0 field strength generated by an MRI-guided radiation delivery system may be significantly smaller, like e.g. 1.5 T or 0.35 T. More subtle effects may include image distortions due to uniformity changes due to differences in penetration of RF fields with different wavelengths, or simply because of different RF receiver coils. Also, differences in gradient coil geometry my lead e.g. to differences in the shapes and severity of fold-over artifacts or to limitations in maximum obtainable field-of-view.

According to embodiments, the execution of the machine executable instructions further causes the magnetic resonance imaging system in the emulation mode to reconstruct the emulated magnetic resonance image using the acquired emulated magnetic resonance imaging data. Embodiments may have the beneficial effect that an emulated magnetic resonance image is provided with imaging characteristics equal to those imaging characteristics of magnetic resonance images reconstructed by the reference imaging system. This may alleviate a comparison of the emulated magnetic resonance image with magnetic resonance images reconstructed by the reference imaging system. For example, it may alleviate registering the emulated magnetic resonance image with magnetic resonance images reconstructed by the reference imaging system.

According to embodiments, the performance of the magnetic field gradient system in the emulation mode is limited by a first performance limitation value defined by the emulation control parameters. The first performance limitation value is smaller than a first performance value defined by the default control parameters. The first performance limitation value mimics a first reference performance value assigned to the reference magnetic resonance imaging system.

Embodiments may have the beneficial effect that the performance of the magnetic field gradient system may be limited in order to mimic the performance of a reference magnetic field gradient system of the reference magnetic resonance imaging system. The reference magnetic field gradient system of the reference magnetic resonance imaging system may only be enabled to achieve a restricted performance relative to the magnetic field gradient system of the magnetic resonance imaging system in default mode, i.e. compared to an available top performance of the magnetic resonance imaging system. This restriction may e.g. be due to additional constraints, the reference MRI system has to meet, e.g. due to additional hardware components like a radiation source.

According to embodiments, the performance of the radio-frequency antenna system in the emulation mode is limited by a second performance limitation value defined by the emulation control parameters. The second performance limitation value is smaller than a second performance value defined by the default control parameters. The second performance limitation value mimics a second reference performance value assigned to the reference magnetic resonance imaging system.

Embodiments may have the beneficial effect that the performance of the radio-frequency antenna system may be limited in order to mimic the performance of a reference radio-frequency antenna system of the reference magnetic resonance imaging system. The reference radio-frequency antenna system of the reference magnetic resonance imaging system may only be enabled to achieve a restricted performance relative to the radio-frequency antenna system of the magnetic resonance imaging system in default mode, i.e. compared to an available top performance of the magnetic resonance imaging system. This restriction may e.g. be due to additional constraints, the reference MRI system has to meet, e.g. due to additional hardware components like a radiation source.

According to embodiments, the set of emulated imaging characteristics comprises one or more of the following: an emulated signal-to-noise-ratio, an emulated image contrast, an emulated image distortion and an emulated chemical shift. Embodiments may have the beneficial effect that the magnetic resonance imaging system operated in the emulation mode using the set of emulation control parameters may provide magnetic resonance imaging data for reconstructing an emulated magnetic resonance image mimicking the signal-to-noise-ratio, the image contrast, the image distortion and/or the chemical shift of MRI images reconstructed using MRI data acquired by the reference imaging system.

According to embodiments, the magnetic resonance imaging system further comprises a white noise RF source. The set of emulation control parameters comprises control parameters for controlling the white noise RF source during acquisition of the emulated magnetic resonance imaging data to generate white noise to reduce the emulated signal-to-noise-ratio resulting from the acquired emulated magnetic resonance imaging data to mimic a reference signal-to-noise-ratio according to the reference imaging characteristics.

Embodiments may have the beneficial effect that the signal-to noise-ratio of emulated MRI images reconstructed using the acquired MRI data may match the signal-to noise-ratio of images reconstructed using MRI data acquired by the reference imaging system. In the default mode, the white noise RF source may be turned off in order to increase the signal-to-noise-ratio of images reconstructed using MRI data acquired in the default operation mode. Thus, the signal-to noise-ratio obtained in the default mode may be higher than the signal-to noise-ratio obtainable in the emulation mode.

According to embodiments, the emulation control parameters comprise emulation pulse sequence commands mimicking reference pulse sequence commands assigned to the reference magnetic resonance imaging system. Embodiments may have the beneficial effect that in the emulation mode pulse sequence commands reference pulse sequence commands may be used which mimic pulse sequence commands acquired by the reference magnetic resonance imaging system. These emulation mode pulse sequence commands may be different from pulse sequence commands comprised by the default control parameters and used in the default mode.

According to embodiments, the emulation control parameters comprise emulation pulse sequence commands defining an emulation repetition time and an emulation echo time. At least one of the emulation repetition time and the emulation echo time is configured to control the acquisition of the emulated magnetic resonance imaging data to adjust the emulated image contrast resulting from the acquired emulated magnetic resonance imaging data to mimic a reference image contrast according to the reference imaging characteristics.

Embodiments may have the beneficial effect that by using a suitable emulation repetition time and/or emulation echo time, emulated magnetic resonance imaging data may be acquired which allows for reconstructing an emulated magnetic resonance image with an emulated image contrast matching a predefined reference image contrast assigned to the reference imaging system.

In MRI, each tissue type returns to its equilibrium state after excitation by the independent processes of T1, i.e. spin-lattice, and T2, i.e. spin-spin, relaxation. In order to generate a T1-weighted image, i.e. an image highlighting tissue types for which T1 relaxation dominates, magnetization is allowed to recover before measuring the MRI signal by suitably controlling the repetition time (TR). In order to generate a T2-weighted image, magnetization is allowed to decay before measuring the MRI signal by suitably controlling the echo time (TE). Thus, by controlling repetition time and echo time used for the data acquisition, the contrast of the resulting image may be controlled. By suitably controlling TR and TE, it may be possible to reach a desired contrast, i.e. a predefined reference image contrast of the reference magnetic imaging system, between any two tissue types with different relaxation behavior. In case the reference image contrast is T1 or T2 weighted, the respective image contrast may effectively be mimicked by adjusting the dominating parameter, i.e. TR or TE, for the acquisition of the emulated magnetic resonance data.

According to embodiments, the emulation control parameters comprise control parameters controlling the magnetic resonance imaging system such that the acquired emulated magnetic resonance imaging data comprise a T1 map and a T2 map to adjust the emulated image contrast resulting from the acquired emulated magnetic resonance imaging data using a combination of the T1 map and the T2 map to mimic the reference image contrast according to the reference imaging characteristics.

Embodiments may have the beneficial effect that by acquiring emulated magnetic resonance data comprising a T1 map as well as a T2 map, it may be possible to reach any desired contrast between any two tissue types with different relaxation behavior using a suitable combination of the T1 map and the T2 map. The combination of the T1 map and the T2 map may e.g. be a linear or a non-linear combination.

According to embodiments, the emulation control parameters comprise control parameters controlling the magnetic resonance imaging system such that the acquired emulated magnetic resonance imaging data provide one or more of the following to adjust the emulated image contrast resulting from the acquired emulated magnetic resonance imaging data to mimic the reference image contrast according to the reference imaging characteristics: a fat suppression and a water suppression.

Embodiments may have the beneficial effect that using fat suppression and/or water suppression, it may be possible to independently reduce the fat signal. Consequently, any desired contribution of fat induced signals to the emulated image contrast may be mimicked. Above, it has been described how to reach a desired contrast between a chosen pair of tissue types with different relaxation behavior controlling T1 and T2 contributions. If neither of these two tissue types is fat, it may additionally be possible to independently reduce the fat induced signal by an arbitrary amount, e.g. by a FatSat pulse with a suitable flip angle less than 90° or by a modified Dixon reconstruction aiming for only partial fat suppression. On the other hand, the fat induced signal may be increased compared to other tissue types by applying a water suppression using e.g. the same aforementioned techniques. Thus, by combining a linear combination of the T1 map and the T2 map with an independent adjustment of the fat induced signal, it may be possible to emulate the contrast of any three tissue types, wherein a single one of these is fat, while the remaining two tissue types display a different relaxation behavior.

For example, the first magnetic resonance imaging data may comprise separate fat MRI data and water MRI data acquired using a Dixon approach, like e.g. a single point or multi-point Dixon approach. Using a combination of those separate fat MRI data and water MRI data, e.g. in form of a separate fat image and water image, any contribution of fat induced signals may be emulated by a combination of the respective two separate datasets.

According to embodiments, the emulation control parameters comprise control parameters controlling the magnetic resonance imaging system to acquire with the emulated magnetic resonance imaging data emulated magnetic field mapping data to compare the emulated magnetic field mapping data with reference magnetic field mapping data assigned to the reference magnetic imaging system and using the result of the comparison to adjust the emulated image distortion resulting from the acquired emulated magnetic resonance imaging data to mimic a reference image distortion according to the reference imaging characteristics. The magnetic field mapping data comprise one or more of the following: a B0 field map and a B1 field map.

Embodiments may have the beneficial effect using a B0 field map and/or a B1 field map, magnetic field inhomogeneities and their effects on the emulated image distortion of emulated magnetic resonance image reconstructed using the emulated magnetic resonance data acquired with the respective B0 and B1 fields may be determined. Thus, the emulated magnetic resonance data or the resulting emulated magnetic resonance image may be adjusted such that they resemble an image distortion corresponding to a reference B0 and/or B1 field map of the reference magnetic resonance imaging system rather than to the actual B0 and/or B1 field map of the magnetic resonance imaging system. The respective reference B0 and/or B1 field map may e.g. be acquired for the reference magnetic resonance imaging system and provided to the magnetic resonance imaging system, e.g. as part of the reference imaging characteristics. In other words, the emulated magnetic resonance data or the resulting emulated magnetic resonance image may be adjusted such that they resemble effects origin from predefined magnetic field inhomogeneities assigned to the reference imaging system.

Image distortion, i.e. distortion of the geometry and/or intensity, of an MRI image may be caused by a lack of homogeneity of the magnetic fields used for acquiring the magnetic resonance data. A source of geometric distortion are e.g. gradient field non-idealities. Homogeneity refers to the uniformity of a magnetic field in the imaging zone of the magnetic resonance imaging system. Magnetic field homogeneity may be measured in parts per million (ppm) over a certain diameter of spherical volume (DSV). Inhomogeneity refers to a degree of lack of homogeneity of the respective magnetic fields, for example a fractional deviation of a local value of the respective magnetic field from an average value of the respective field.

A general goal, when designing and manufacturing an MRI system, is achieve a magnetic field as homogeneous as possible, especially at the core of the scanner. However, even with an ideal magnet, some intrinsic inhomogeneities may always remain, while additional inhomogeneities may be caused by the susceptibility of a subject which is positioned in the magnetic field and from which the magnetic resonance imaging data is acquired. The geometrical distortion refers to a displacement of pixel locations. Intensity distortion refers to an undesired change in the intensity or brightness of pixels/voxels, which may cause problems in determining different tissues and reduce the maximum achievable image resolution.

Such inhomogeneity effects may be compensated by post-processing using a B0 map. The B0 map may be used to adjust the emulated image distortion and to match the reference image distortion. The B0 map may e.g. be acquired by a low-resolution coarse calibration reference scan. Furthermore, emulating the image distortions of the reference system or even the knowledge of these distortions may have the beneficial effect that the user may be able to observe whether a patient is too large for the (optimal) imaging volume of the reference MRI system already during usage of the emulation mode, e.g. during a radiotherapy simulation before sending the patient to a MRI-guided LINAC. The useful imaging FOV may well differ between different MRI systems, in particular between an exclusive MRI system and an MRI-guided medical system like e.g. an MRI-guided LINAC.

Spatial inhomogeneity of the B1 field, i.e. the magnetic field produced by the radio frequency coils, may e.g. case flip-angle deviations depending on the spatial position which may result in a reduced signal in these areas or an altered contrast. Such B1 inhomogeneity may e.g. arise, because the RF power is absorbed differently across the subject, due to the changing permittivity and conductivity of tissues, i.e. dielectric effects, and standing waves in tissues.

Using for example a plurality of coils, e.g. in form a phased-array coil in conjunction with parallel imaging, placed in the near vicinity or on the subject, may enable a higher SNR, but may simultaneously result in a non-uniformity of signal. The depth of penetration of coils is inversely proportional to their diameters. For small coils, this may lead to an accentuation of signals arising superficially in the subject, while signals arising deep in the subject are attenuated.

For multichannel parallel imaging it may be possible to make corrections for non-uniform receiver coil profiles using coil sensitivity maps acquired by a coil sensitivity calibration pre-scan. There are different methods known for performing such corrections based on a pre-scan, like e.g. PURE ("Phased array Uniformity Enhancement"), Prescan Normalize, CLEAR ("Constant LEvel AppeaRance") or NATURAL ("NATural Uniformity Realization Algorithm").

Distortions due to non-uniformity of the B1 magnetic field caused by receiver coil geometry, i.e. non-uniformity due to receiving, may e.g. be reduced using CLEAR reconstruction technique. Furthermore, distortions due to non-uniformity of the transmission coil geometry may be reduced as well using CLEAR. The image uniformity because of transmission may be determined by B1 mapping. If B1 mapping is performed for the magnetic resonance imaging system as well as for the reference magnetic resonance imaging system, CLEAR reconstructed emulation images may be modified in reconstruction with this information either to remove the non-uniformity due to transmission for both MRI systems or to set the non-uniformity of the MRI system to correspond to the non-uniformity of the reference MRI system. In particular, the image distortion of the emulated magnetic resonance data, e.g. using CLEAR, may be adjusted to generate an emulated image distortion matching the image distortion of magnetic resonance images of the reference MRI system.

The B1 map may thus be used by the MRI system to adjust the emulated image distortion and to match the reference image distortion. The B1 map may e.g. be acquired by a low-resolution coarse calibration reference scan.

According to embodiments, the emulation control parameters comprise control parameters controlling magnetic resonance imaging system to adjust an emulation bandwidth of the magnetic resonance system for acquiring the emulated magnetic resonance imaging data to mimic a reference bandwidth assigned to the reference magnetic resonance imaging system to adjust the emulated chemical shift resulting from the acquired emulated magnetic resonance imaging data to mimic a reference chemical shift according to the reference imaging characteristics.

Embodiments may have the beneficial effect that the signal bandwidth for acquiring the emulated magnetic resonance data may be controlled to match the predefined chemical shift and predefined image distortion assigned to the reference magnetic resonance imaging system.

For example, narrow receive bandwidths accentuate the water fat shift, i.e. the frequency bandwidth resulting in pixel shift due to the water/fat spectral separation, by assigning a smaller number of frequencies across the MRI image. since the amount of water fat shift is proportional to the main magnetic field, this effect is much more significant on higher field strengths. At 1.5 T, fat and water precess 220 Hz apart, which results in a higher shift than in lower field MRI.

Chemical shift refers to small changes in resonant frequency due to different molecular environments of nuclei. The resonance frequency of a particular nucleus is determined not by the strength of the externally applied magnetic field, but by the resulting local field experienced by the nucleus at the atomic level. All $^1$H nuclei within a patient therefore do not resonate at precisely the same frequency. Differences in resonance frequency referred to as chemical shifts exist depending upon the chemical nature of the molecule in which they reside.

In case a system frequency is set to a resonance frequency of a first chemical component, signals from a second chemical component with a lower resonance frequency due to the chemical shift may appear to arise from the first chemical component located at another voxel in a lower part of the field. When image intensities are assigned in a reconstructed MRI image, the location of the second component may thus be spatially mismapped toward the lower part of the readout gradient field. The result of this mismapping may be a chemical shift artifact, e.g. in form of white or dark bands.

The size of the chemical shift artifact depends on the receiver bandwidth and the size of the frequency-encode matrix. Reducing the bandwidth per pixel accentuates chemical shift artifact, while increasing the bandwidth per pixel alleviates it.

Herein, bandwidth (BW) refers to the range of frequencies involved in the reception of the magnetic resonance imaging data from the imaging zone by the radio-frequency antenna system. Frequency encoding using a spatially varying gradient results in a variation of precision frequencies along the gradient. Thus, the resonances may vary, wherein the range of the variation is referred to as the total bandwidth, i.e. total receiver BW. The total receiver BW may generally range from about 5 kHz to 100 kHz. A typical value for the receiver BW may e.g. be 50 kHz.

According to embodiments, a magnetic field strength of the main magnetic field generated by the main magnet of the magnetic resonance imaging system in the default mode is larger than a reference magnetic field strength of a main magnetic field assigned to the reference magnetic resonance imaging system. Embodiments may have the beneficial effect that by operating the magnetic resonance imaging system in the emulation mode emulated magnetic resonance data may be acquired and emulated magnetic resonance images may be reconstructed which match predefined imaging characteristics assigned to a reference magnetic resonance imaging system with a smaller magnetic field strength of the main magnetic field. Thus, effects of a smaller magnetic field strength may be effectively mimicked. The first magnetic field strength may e.g. be a 3 T, while the magnetic field strength may e.g. be 1.5 T or even as small as 0.35 T.

Embodiments relate to an MRI system used in medical departments, i.e. diagnostic departments. The reference magnetic resonance imaging system e.g. may comprise a radiation source configured for applying one of the following to a target located within the imaging zone: X-rays and gamma rays. The radiation source may e.g. be provided by a LINAC or $^{60}$Co radionuclides. Thus, the reference magnetic reference imaging system may be an MRI system used in radiotherapy departments comprising a radiation delivery system.

According to embodiments, furthermore a post-processing filtering operation may be applied to the emulated magnetic resonance imaging data to further improve the mimicking of the reference imaging characteristics. The post-processing filtering may comprise adding noise to the acquired emulated magnetic resonance imaging data in order to (further) reduce the emulated signal-to-noise-ratio and to match a lower reference signal-to-noise-ratio. According to embodiments, the SNR may be artificially reduced e.g. by adding Gaussian noise to the image data in the reconstruction. According to further embodiments, the SNR may be improved to match a higher reference signal-to-noise-ratio using signal averaging, i.e. by averaging over a plurality of emulated magnetic resonance imaging data acquired for identical sampling points.

According to embodiments, the acquired emulated magnetic resonance imaging data and/or the reconstructed emulated magnetic resonance image may be provided to the reference imaging system. The reconstructed emulated magnetic resonance image may be designated to be registered with one or more magnetic resonance images reconstructed using magnetic resonance data acquired by the reference magnetic resonance imaging system. Based on the registration a different position and/or orientation of an anatomical structure of according to the magnetic resonance data acquired by the reference magnetic resonance imaging system relative to a reference position and/or orientation defined using the emulated magnetic resonance data may be determined. For example, it may be determined whether and how a current position and/or orientation deviates from a position and/or orientation which forms the basis of a dose plan to be executed by a radiation delivery system.

The emulated magnetic resonance image may e.g. be used for simulating a radiation delivery using a radiation delivery system and/or for establishing a dose plan. The reference magnetic resonance imaging system may e.g. be used for aligning a patient for executing the dose plan. Aligning a patient for execution of a dose plan may be the more facilitated, the more magnetic resonance images used for preparing the dose plan, i.e. for deveining target areas and organs of risk, matches the magnetic resonance images acquired by the radiation delivery system. The comparison between the emulated magnetic resonance image and a magnetic resonance image obtained by the reference magnetic resonance imaging system may comprise determining adjustment parameters for adjusting a dose plan for applying a radiation dose to a target comprised by the anatomical structure of interest. The adjustment parameters may be configured to compensate for differences between the spatial reference position of the anatomical structure for which the dose plan is defined and the current position of the anatomical structure of interest as determined by the reference magnetic resonance imaging system.

In another aspect, the invention relates to a method for controlling a magnetic resonance imaging system. The magnetic resonance imaging system comprises a main magnet for generating a main magnetic field within an imaging zone of the magnetic resonance imaging system, a magnetic field gradient system for generating a spatially dependent gradient magnetic field within the imaging zone, a radio-frequency antenna system configured for acquiring magnetic resonance imaging data from the imaging zone.

The magnetic resonance imaging system further comprises a memory storing machine executable instructions, a set of default control parameters for operating the magnetic resonance imaging system in a default mode for acquiring magnetic resonance imaging data for reconstructing a magnetic resonance image with a set of default imaging characteristics and a set of emulation control parameters for operating the magnetic resonance imaging system in an emulation mode for acquiring emulated magnetic resonance imaging data for reconstructing an emulated magnetic resonance image with a set of emulated imaging characteristics mimicking a set of reference imaging characteristics assigned to a reference magnetic resonance imaging system. The reference imaging characteristics differ from the default imaging characteristics.

The magnetic resonance imaging system further comprises a processor. Execution of the machine executable instructions by the processor causes the processor to execute the method. The method comprises receiving a selection signal selecting the emulation mode. The magnetic resonance imaging system is switched from the default mode to the emulation mode. The magnetic resonance imaging system is operated in the emulation mode using the set of emulation control parameters. The emulated magnetic resonance imaging data is acquired from the imaging zone of the magnetic resonance imaging system.

In another aspect, the invention relates to a computer program product comprising machine executable instructions for execution by a processor controlling a magnetic resonance imaging system. The magnetic resonance imaging system comprises a main magnet for generating a main magnetic field within an imaging zone of the magnetic resonance imaging system, a magnetic field gradient system for generating a spatially dependent gradient magnetic field within the imaging zone, a radio-frequency antenna system configured for acquiring magnetic resonance imaging data from the imaging zone.

The magnetic resonance imaging system further comprises a memory for storing a set of default control parameters for operating the magnetic resonance imaging system in a default mode for acquiring magnetic resonance imaging data for reconstructing a magnetic resonance image with a set of default imaging characteristics and a set of emulation control parameters for operating the magnetic resonance imaging system in an emulation mode for acquiring emulated magnetic resonance imaging data for reconstructing an emulated magnetic resonance image with a set of emulated imaging characteristics mimicking a set of reference imaging characteristics assigned to a reference magnetic resonance imaging system. The reference imaging characteristics differ from the default imaging characteristics.

Execution of the machine executable instructions by the processor causes the processor to execute the method. The method comprises receiving a selection signal selecting the emulation mode. The magnetic resonance imaging system is switched from the default mode to the emulation mode. The magnetic resonance imaging system is operated in the emulation mode using the set of emulation control parameters. The emulated magnetic resonance imaging data is acquired from the imaging zone of the magnetic resonance imaging system.

According to embodiments, the computer program product may further comprise the set of default control parameters, the set of emulation control parameters and/or the set of reference imaging characteristics assigned to a reference magnetic resonance imaging system. According to embodiments, the set of default control parameters, the set of emulation control parameters and/or the set of reference imaging characteristics assigned to a reference magnetic resonance imaging system may be stored in the memory of the magnetic resonance imaging system.

The aforementioned embodiments of the invention may enable to operate an MRI system in at least two different modes, i.e. a default mode and an emulation mode. The default control parameters controlling MRI data acquisition in the default mode may be optimized inter alia based on hardware features of the MRI system in order to optimize imaging quality of the resulting MRI images. The emulation control parameters controlling MRI data acquisition in the emulation mode may be optimized in order to match predefined imaging characteristics assigned to a reference magnetic resonance imaging system.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator. A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by nuclear spins using the antenna of a Magnetic resonance apparatus during a magnetic resonance imaging scan. A Magnetic Resonance Imaging (MRI) image or MR image is defined herein as being the reconstructed two or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
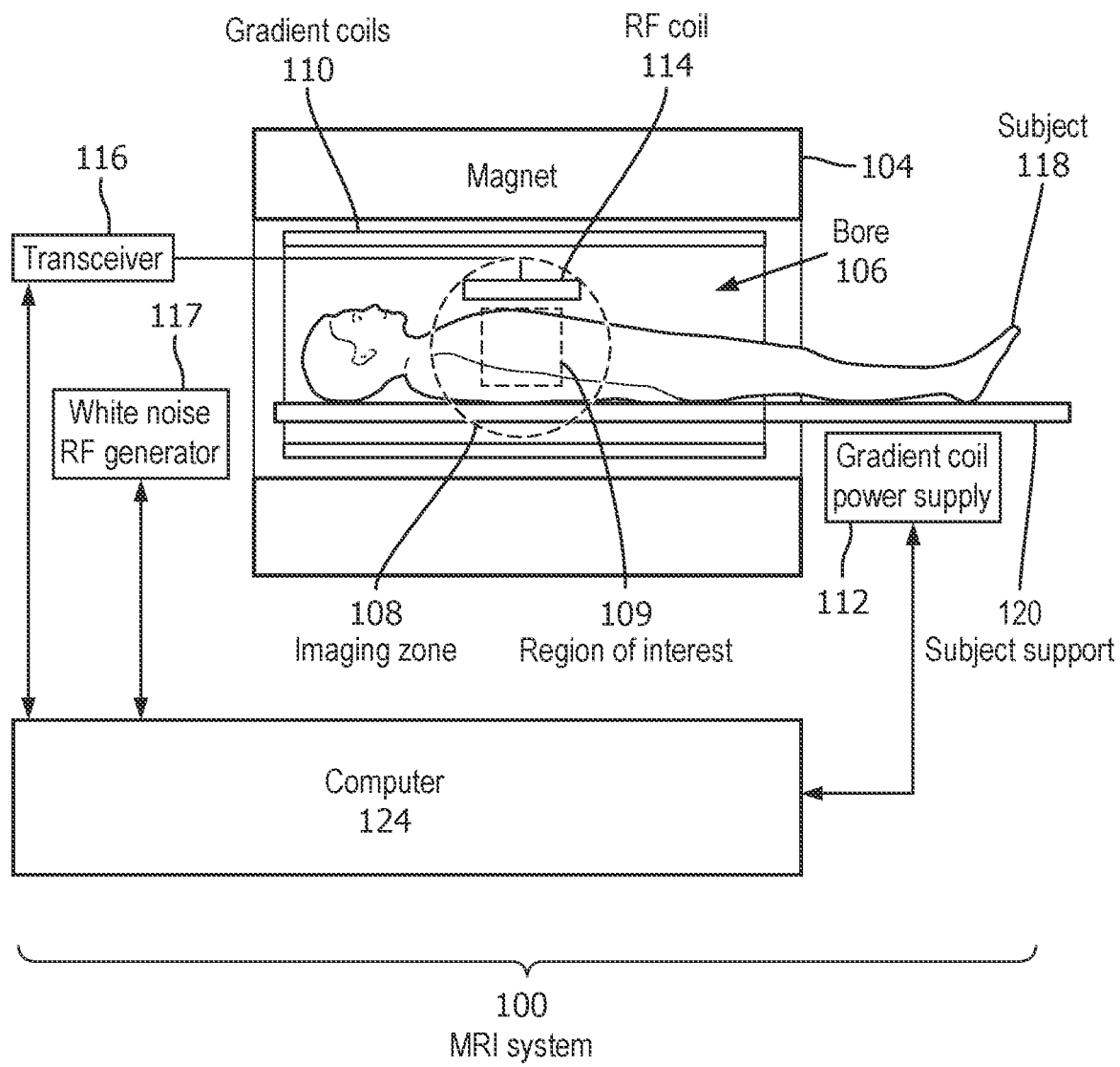
FIG. 1 shows an example of a magnetic resonance imaging system.

FIG. 1 shows an example of a magnetic resonance imaging system 100 for acquiring the emulated magnetic resonance imaging data. The magnetic resonance imaging system 100 may be configured to be operated in a default mode for acquiring magnetic resonance imaging data as well as in an emulation mode for acquiring emulated resonance imaging data. The magnetic resonance imaging system 100 comprises a magnet 104. The magnet 104 is a superconducting cylindrical type magnet with a bore 106 through it. The use of different types of magnets is also possible. For instance, it is also possible to use both a split cylindrical magnet and a so called open magnet. A split cylindrical magnet is similar to a standard cylindrical magnet, except that the cryostat has been split into two sections to allow access to the axial plane through the iso-center of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance data is typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise, the transceiver 116 may also represent a separate transmitter and separate receivers. The radio-frequency coil 114 may also have multiple receive/transmit elements and the radio frequency transceiver 116 may have multiple receive/transmit channels. For example, if a parallel imaging technique such as SENSE is performed, the radio-frequency could 114 will have multiple coil elements.

The magnetic resonance imaging system 100 furthermore comprises a white noise RF generator 117 for generating white noise. When activating the white noise RF generator 117 is generated in the emulation mode, white noise is generated increasing the noise of the system and thus reducing the SNR of the emulated magnetic resonance imaging data. According to embodiments, the white noise RF generator 117 may be deactivated during the default mode.

The transceiver 116, the gradient controller 112, and the white noise RF generator 117 are shown as being connected to a computer 124 of the magnetic resonance imaging system 100. An example of the computer 124 is shown in more detail in FIG. 2.

Figure 2:
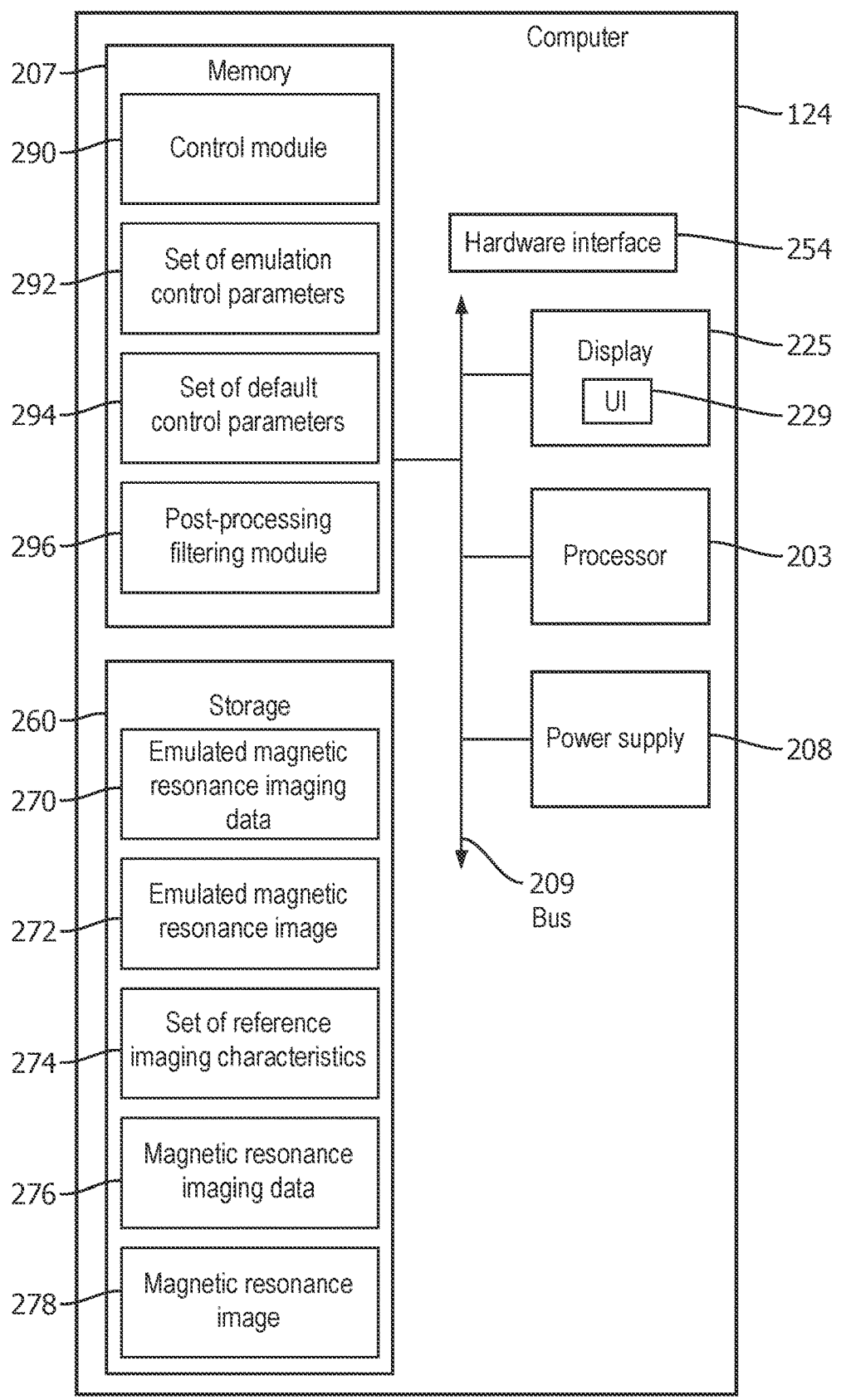
FIG. 2 shows an example of a computer of the magnetic resonance imaging system of FIG. 1.

FIG. 2 shows an example of the computer 124 comprised by the magnetic resonance imaging system 100 of FIG. 1. The computer 124 comprises a processor 203, a memory 207 each capable of communicating with one or more components of the magnetic resonance imaging system 100, like e.g. transceiver 116, gradient controller 112, and white noise RF generator 117. For example, the components of the magnetic resonance imaging system 100 are coupled to a bidirectional system bus 209.

It will be appreciated that the methods described herein are at least partly non-interactive, and automated by way of computerized systems. For example, these methods can further be implemented in software, (including firmware), hardware, or a combination thereof. In exemplary embodiments, the methods described herein are implemented in software, as an executable program. The computer 124 may be a special or general-purpose digital computer, such as a personal computer, workstation, minicomputer, or mainframe computer.

The processor 203 is a hardware device for executing software, particularly that stored in memory 207. The processor 203 may be any custom made or commercially available processor, a central processing unit (CPU), an auxiliary processor among several processors associated with the computer 124, a semiconductor-based microprocessor (in the form of a microchip or chip set), a macroprocessor, or generally any device for executing software instructions. The processor 203 may control the operation of the magnetic resonance imaging system 100, i.e. the components comprised by the magnetic resonance imaging system 100 to which the processor 203 is operatively connected e.g. via a hardware interface 254.

The memory 207 may include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM)). Note that the memory 207 may have a distributed architecture, where various components are situated remote from one another, but are accessible by the processor 203. Memory 207 may store machine readable instructions, e.g. in form of a control module 290 for controlling the MRI system 100.

The computer 124 may further comprise a display device 225 which displays characters and images and the like e.g. on a user interface 229. The display device 225 may e.g. be a touch screen display device.

The computer 124 may further comprise a power supply 208 for powering the computer 124. The power supply 208 may for example be a battery or an external source of power, such as electricity supplied by a standard AC outlet.

The connection between hardware interface 254 and the further components of the MRI system may for example comprise a BUS Ethernet connection, WAN connection, Internet connection etc.

The processor 203 may be adapted to acquire magnetic resonance imaging data using the MRI system 100 in a compatible digital form so that such magnetic resonance imaging data may be processed and magnetic resonance images reconstructed from the received MRI data may be displayed on the display device 225. Furthermore, additional information may be received from the further components of the MRI system 100 in a compatible digital form so that it may be displayed on the display device 225. Such additional information may include operating parameters, alarm notifications, and other information related to the use, operation and function of the MRI system 100.

Storage device 260 is shown as containing emulated magnetic resonance imaging data 270 that has been acquired by the magnetic resonance imaging system 100 operated in the emulation mode. An emulated magnetic resonance image 272 is reconstructed from the emulated magnetic resonance imaging data 270 with a set of emulated imaging characteristics mimicking a set of reference imaging characteristics 274 assigned to a reference magnetic resonance imaging system. The emulated magnetic resonance image 272 may e.g. be used for radiation delivery simulation and/or establishing a dose plan. This usage of the magnetic resonance image 272 may e.g. be performed by the magnetic resonance imaging system 100 or by an additional magnetic resonance imaging data processing system to which the magnetic resonance image 272 is sent. In addition or alternatively, the emulated magnetic resonance image 272 may e.g. be sent to the reference magnetic resonance imaging system. The emulated set of imaging characteristics comprises one or more of the following: an emulated signal-to-noise-ratio, an emulated image contrast, an emulated image distortion and an emulated chemical shift. The storage device 260 is shown as further containing further magnetic resonance imaging data 276 acquired by the magnetic resonance imaging system 100 operated in the default mode. A further magnetic resonance image 278 is reconstructed from the magnetic resonance imaging data 276 acquired in the default mode with a set of default imaging characteristics. The reference imaging characteristics 274 differ from the default imaging characteristics.

The memory 207 is shown as containing a control module 290 with machine executable instructions for controlling the magnetic resonance imaging system 100, when being executed by the processor 203. The memory 207 is further shown as containing a set of emulation control parameters 292 for operating the magnetic resonance imaging system 100 in the emulation mode for acquiring the emulated magnetic resonance imaging data 270 and reconstructing the emulated magnetic resonance image 272. In the emulation mode, the magnetic resonance imaging system 100 is operated by the control module 290 using the set of emulation control parameters 292. The memory 207 is further shown as containing a set of default control parameters 294 for operating the magnetic resonance imaging system 100 in a default mode for acquiring the magnetic resonance imaging data 276 and reconstructing the magnetic resonance image 278. In the default mode, the magnetic resonance imaging system 100 is operated by the control module 290 using the set of default control parameters 294.

According to embodiments, the memory may furthermore comprise a post-processing filtering module 296 for further matching the emulated imaging characteristics of the emulated magnetic resonance image 272 with the set of reference imaging characteristics 274 using post-processing of the acquired emulated magnetic resonance imaging data 270.

The computer 124 and the MRI system 100 may or may not be an integral part. In other terms, the computer 124 may or may not be external to the MRI system 100. The MRI system 100 may comprise components that are controlled by the processor 203 in order to configure the MRI system 100. The configuration of the MRI system 100 may enable the operation of the respective MRI system, i.e. acquiring magnetic resonance imaging data. The operation of the MRI system 100 may for example be automatic. The MRI system 100 may be configured to provide output data such as the emulated magnetic resonance imaging data 270 or the magnetic resonance imaging data 276 to computer 124 in response to a magnetic resonance imaging data acquisition instruction executed by the processor 203.

Figure 3:
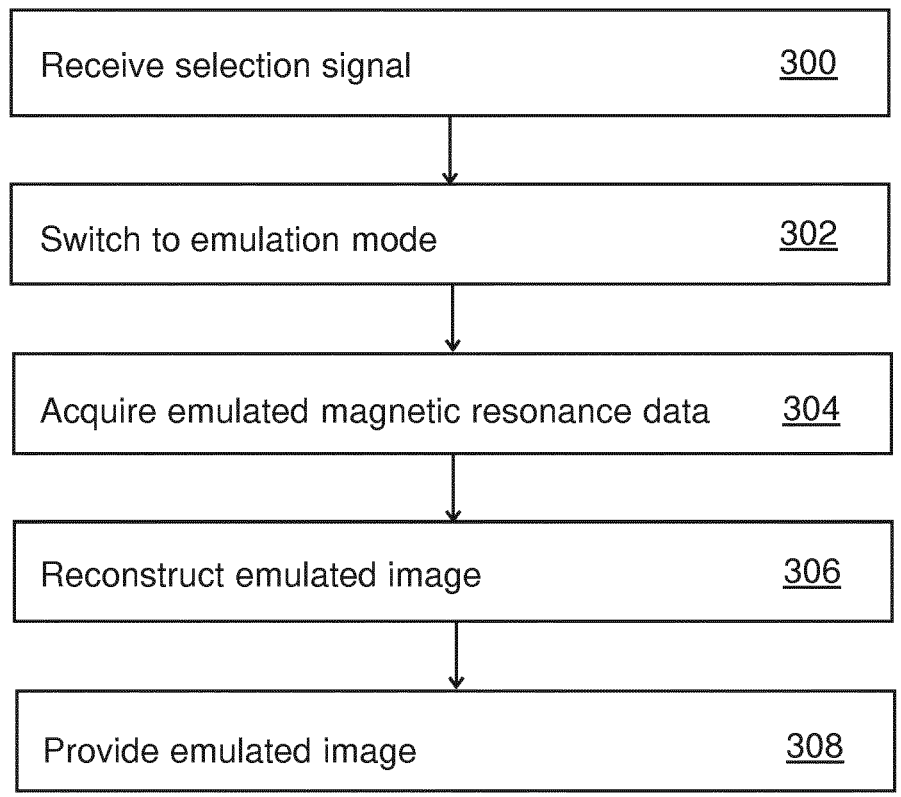
FIG. 3 illustrates an exemplary method of controlling the magnetic resonance imaging system of FIG. 1.

FIG. 3 shows a flowchart which illustrates an exemplary method of controlling the magnetic resonance imaging system 100 of FIG. 1. In step 300, the magnetic resonance imaging system receives a selection signal selecting the emulation mode. For example, a menu may be provided on a display of a user interface, enabling the user to select between a default mode and an emulation. In step 302, the magnetic resonance imaging system is switched from the default mode to the emulation mode. In the emulation mode, the magnetic resonance imaging system is operated using a set of emulation control parameters. In step 304, the emulated magnetic resonance imaging data is acquired from the imaging zone of the magnetic resonance imaging system using the emulation control parameters. In step 306, an emulated magnetic resonance image is reconstructed using the emulated magnetic resonance imaging data acquired in step 304. The emulated magnetic resonance image reconstructed in step 308 has a set of emulated imaging characteristics mimicking a set of reference imaging characteristics assigned to a reference magnetic resonance imaging system. The reference imaging characteristics differ from default imaging characteristics of magnetic resonance images reconstructed from magnetic resonance imaging data acquired in a default mode by the magnetic resonance imaging system. In the default mode, the magnetic resonance imaging system is operated using a set of default control parameters rather than the emulation control parameters. The set of emulated imaging characteristics may comprise one or more of the following: an emulated signal-to-noise-ratio, an emulated image contrast, an emulated image distortion and an emulated chemical shift. In step 308, the emulated magnetic resonance image reconstructed in step 306 is provided e.g. to the reference magnetic resonance imagining system in order to be compared with magnetic resonances images reconstructed from magnetic resonance data acquired by the reference magnetic resonance imagining system.

Figure 4:
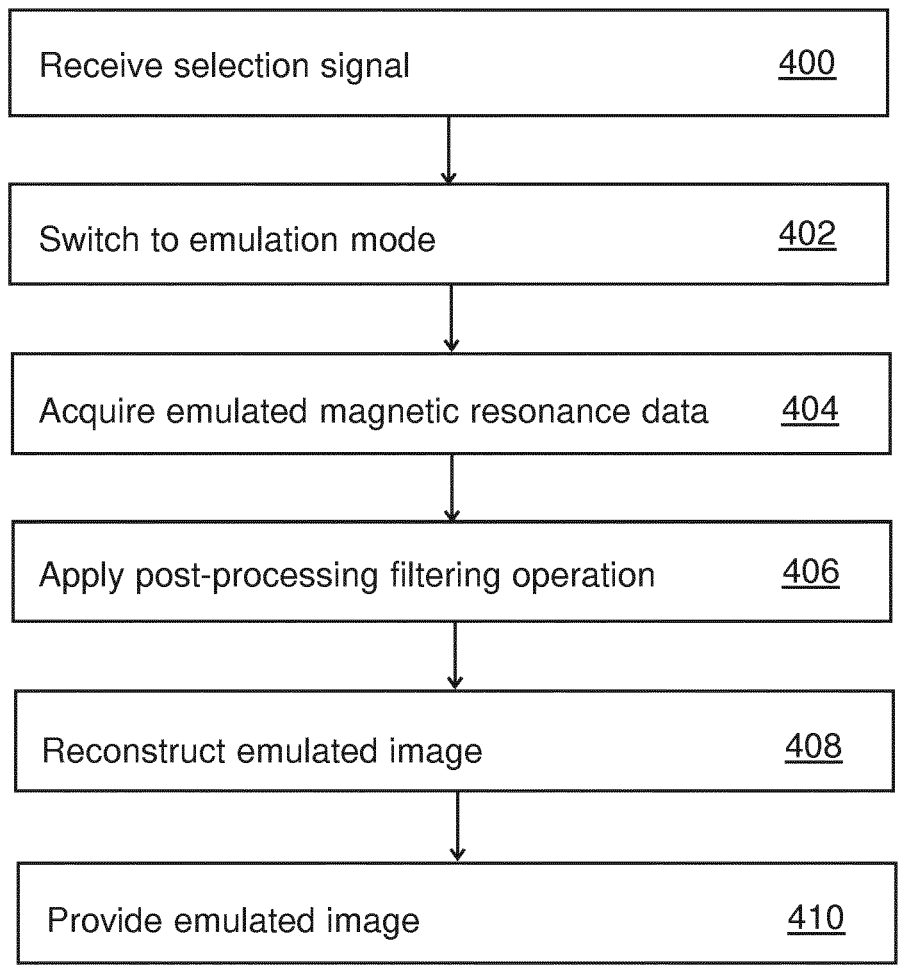
FIG. 4 illustrates an exemplary method of controlling the magnetic resonance imaging processing system of FIG. 1

FIG. 4 shows a flowchart which illustrates a further exemplary method of controlling the magnetic resonance imaging system 100 of FIG. 1. Steps 400 to 404 and 408 to 410 correspond to steps 300 to 308 of FIG. 3. In addition, the method of FIG. 4 comprises step 406. In step 406, a post-processing filtering operation is applied to the emulated magnetic resonance imaging data acquired in step 404. By the post-processing, the emulated magnetic resonance imaging data may be adjusted to result in an emulated magnetic resonance image with emulated imaging characteristics more accurately matching the predefined reference imaging characteristics of magnetic resonance images reconstructed using magnetic resonance data acquired by the magnetic resonance imaging system.

Further embodiments and aspects of the invention comprise
2. The magnetic resonance imaging system (100) of claim 1, wherein the execution of the machine executable instructions (290) further causes the magnetic resonance imaging system (100) in the emulation mode to reconstruct the emulated magnetic resonance image (272) using the acquired emulated magnetic resonance imaging data (270).
14. A method for controlling a magnetic resonance imaging system (100), the magnetic resonance imaging system (100) comprising:

a main magnet (104) for generating a main magnetic field within an imaging zone (108) of the magnetic resonance imaging system (100), a magnetic field gradient system (110) for generating a spatially dependent gradient magnetic field within the imaging zone (108), a radio-frequency antenna system (114) configured for acquiring magnetic resonance imaging data from the imaging zone (108), a memory (207) storing machine executable instructions (290), a set of default control parameters (294) for operating the magnetic resonance imaging system (100) in a default mode for acquiring magnetic resonance imaging data (276) for reconstructing a magnetic resonance image (278) with a set of default imaging characteristics, a set of emulation control parameters (292) for operating the magnetic resonance imaging system (100) in an emulation mode for acquiring emulated magnetic resonance imaging data (270) for reconstructing an emulated magnetic resonance image (272) with a set of emulated imaging characteristics mimicking a set of reference imaging characteristics (274) assigned to a reference magnetic resonance imaging system, wherein the reference imaging characteristics (274) differ from the default imaging characteristics, a processor (203), wherein execution of the machine executable instructions (290) by the processor (203) causes the processor (203) to execute the method, the method comprising:

receiving a selection signal selecting the emulation mode,
switching from the default mode to the emulation mode,
acquiring the emulated magnetic resonance imaging data (270) from the imaging zone (108) of the magnetic resonance imaging system (100), wherein the magnetic resonance imaging system (100) is operated in the emulation mode using the set of emulation control parameters (292).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
117 white noise RF generator
118 subject
120 subject support
124 computer
203 processor
207 memory
208 power supply
209 bus
225 display
229 user interface
254 hardware interface
260 storage
270 emulated magnetic resonance imaging data
272 emulated magnetic resonance image
274 set of reference imaging characteristics
276 magnetic resonance imaging data
278 magnetic resonance image
290 control module
292 set of emulation control parameters
294 set of default control parameters
296 post-processing filtering module

The invention claimed is:

1. A magnetic resonance imaging system, the magnetic resonance imaging system comprising:

a main magnet for generating a main magnetic field within an imaging zone of the magnetic resonance imaging system, a magnetic field gradient system for generating a spatially dependent gradient magnetic field within the imaging zone, a radio-frequency antenna system configured for acquiring magnetic resonance imaging data from the imaging zone, a memory configured to store machine executable instructions, a set of default control parameters for operating the magnetic resonance imaging system in a default mode for acquiring magnetic resonance imaging data for reconstructing a magnetic resonance image with a set of default imaging characteristics, wherein the default imaging characteristics are optimized for diagnostic imaging of an anatomical structure of interest, a set of emulation control parameters for operating the magnetic resonance imaging system in an emulation mode for acquiring emulated magnetic resonance imaging data for reconstructing an emulated magnetic resonance image with a set of emulated imaging characteristics mimicking a set of reference imaging characteristics assigned to a reference magnetic resonance imaging system, wherein the set of emulated imaging characteristics comprises an emulated signal-to-noise ratio, wherein the reference imaging characteristics differ from the default imaging characteristics, wherein the image quality achievable with the magnetic resonance imaging system is higher than the image quality achievable with the reference magnetic resonance imaging system, wherein the higher image quality comprises a higher signal-to-noise ratio;

a processor, wherein execution of the machine executable instructions by the processor causes the processor to control the magnetic resonance imaging system to:
receive a selection signal selecting the emulation mode,
switch from the default mode to the emulation mode, acquire the emulated magnetic resonance imaging data from the imaging zone of the magnetic resonance imaging system, wherein the magnetic resonance imaging system is operated in the emulation mode using the set of emulation control parameters wherein the magnetic resonance imaging system further comprises a white noise RF source, wherein the set of emulation control parameters comprises control parameters for controlling the white noise RF source during acquisition of the emulated magnetic resonance imaging data to generate white noise to reduce the emulated signal-to-noise-ratio resulting from the acquired emulated magnetic resonance imaging data to mimic a reference signal-to noise-ratio according to the reference imaging characteristics, while the white noise RF source is turned off in the default operation mode in order to increase the signal-to-noise-ratio of the magnetic resonance imaging data acquired in the default operation mode.

2. The magnetic resonance imaging system of claim 1, wherein the reference magnetic resonance imaging system is comprised in an MRI guided radiation delivery system.

3. The magnetic resonance imaging system of claim 2, wherein the reference magnetic resonance imaging system has a field strength of 0.35 or 1.5 T.

4. The magnetic resonance imaging system of claim 1, wherein the performance of the magnetic field gradient system in the emulation mode is limited by a first performance limitation value defined by the emulation control parameters, wherein the first performance limitation value is smaller than a first performance value defined by the default control parameters, wherein the first performance limitation value mimics a first reference performance value assigned to the reference magnetic resonance imaging system.

5. The magnetic resonance imaging system of claim 1, wherein the performance of the radio-frequency antenna system in the emulation mode is limited by a second performance limitation value defined by the emulation control parameters, wherein the second performance limitation value is smaller than a second performance value defined by the default control parameters, wherein the second performance limitation value mimics a second reference performance value assigned to the reference magnetic resonance imaging system.

6. The magnetic resonance imaging system of claim 1, wherein the set of emulated imaging characteristics further comprises one or more of the following: an emulated image contrast, an emulated image distortion and an emulated chemical shift.

7. The magnetic resonance imaging system of claim 6, wherein the emulation control parameters comprise emulation pulse sequence commands defining an emulation repetition time and an emulation echo time, wherein at least one of the emulation repetition time and the emulation echo time is configured to control the acquisition of the emulated magnetic resonance imaging data to adjust the emulated image contrast resulting from the acquired emulated magnetic resonance imaging data to mimic a reference image contrast according to the reference imaging characteristics.

8. The magnetic resonance imaging system of claim 6, wherein the emulation control parameters comprise control parameters controlling the magnetic resonance imaging system such that the acquired emulated magnetic resonance imaging data comprise a T1 map and a T2 map to adjust the emulated image contrast resulting from the acquired emulated magnetic resonance imaging data using a combination of the T1 map and the T2 map to mimic the reference image contrast according to the reference imaging characteristics.

9. The magnetic resonance imaging system of claim 6, wherein the emulation control parameters comprise control parameters controlling the magnetic resonance imaging system such that the acquired emulated magnetic resonance imaging data provide one or more of the following to adjust the emulated image contrast resulting from the acquired emulated magnetic resonance imaging data to mimic the reference image contrast according to the reference imaging characteristics: a fat suppression and a water suppression.

10. The magnetic resonance imaging system of claim 6, wherein the emulation control parameters comprise control parameters controlling the magnetic resonance imaging system to acquire with the emulated magnetic resonance imaging data emulated magnetic field mapping data to compare the emulated magnetic field mapping data with reference magnetic field mapping data assigned to the reference magnetic imaging system and using the result of the comparison to adjust the emulated image distortion resulting from the acquired emulated magnetic resonance imaging data to mimic a reference image distortion according to the reference imaging characteristics, wherein the magnetic field mapping data comprise one or more of the following: a B0 field map and a B1 field map.

11. The magnetic resonance imaging system of claim 6, wherein the emulation control parameters comprise control parameters controlling magnetic resonance imaging system to adjust an emulation bandwidth of the magnetic resonance system for acquiring the emulated magnetic resonance imaging data to mimic a reference bandwidth assigned to the reference magnetic resonance imaging system to adjust the emulated chemical shift resulting from the acquired emulated magnetic resonance imaging data to mimic a reference chemical shift according to the reference imaging characteristics.

12. The magnetic resonance imaging system of claim 1, wherein a magnetic field strength of the main magnetic field generated by the main magnet of the magnetic resonance imaging system in the default mode is larger than a reference magnetic field strength of a main magnetic field assigned to the reference magnetic resonance imaging system.

13. The magnetic resonance imaging system of claim 1 wherein the emulation control parameters comprise emulation pulse sequence commands mimicking reference pulse sequence commands assigned to the reference magnetic resonance imaging system.

14. A computer program product comprising machine executable instructions for execution by a processor controlling a magnetic resonance imaging system, the magnetic resonance imaging system comprising:

a main magnet for generating a main magnetic field within an imaging zone of the magnetic resonance imaging system, a magnetic field gradient system for generating a spatially dependent gradient magnetic field within the imaging zone, a radio-frequency antenna system configured for acquiring magnetic resonance imaging data from the imaging zone, a memory for storing a set of default control parameters for operating the magnetic resonance imaging system in a default mode for acquiring magnetic resonance imaging data for reconstructing a magnetic resonance image with a set of default imaging characteristics, wherein the default imaging characteristics are optimized for diagnostic imaging of an anatomical structure of interest, a set of emulation control parameters for operating the magnetic resonance imaging system in an emulation mode for acquiring emulated magnetic resonance imaging data for reconstructing an emulated magnetic resonance image with a set of emulated imaging characteristics mimicking a set of reference imaging characteristics assigned to a reference magnetic resonance imaging system, wherein the set of emulated imaging characteristics comprises an emulated signal-to-noise ratio, wherein the reference imaging characteristics differ from the default imaging characteristics, wherein the image quality achievable with the magnetic resonance imaging system is higher than the image quality achievable with the reference magnetic resonance imaging system, wherein the higher image quality comprises a higher signal-to-noise ratio;

wherein execution of the machine executable instructions by the processor causes the processor to control the magnetic resonance imaging system to:

receive a selection signal selecting the emulation mode, switch from the default mode to the emulation mode, acquire the emulated magnetic resonance imaging data from the imaging zone of the magnetic resonance imaging system, wherein the magnetic resonance imaging system is operated in the emulation mode using the set of emulation control parameters wherein the magnetic resonance imaging system further comprises a white noise RF source, wherein the set of emulation control parameters comprises control parameters for controlling the white noise RF source during acquisition of the emulated magnetic resonance imaging data to generate white noise to reduce the emulated signal-to-noise-ratio resulting from the acquired emulated magnetic resonance imaging data to mimic a reference signal-to noise-ratio according to the reference imaging characteristics, while the white noise RF source is turned off in the default operation mode in order to increase the signal-to-noise-ratio of the magnetic resonance imaging data acquired in the default operation mode.

* * * * *